(12) United States Patent
Bauer

(10) Patent No.: US 6,749,576 B2
(45) Date of Patent: Jun. 15, 2004

(54) BIOPSY DEVICE WITH ADJUSTABLE SAMPLING

(75) Inventor: Alberto Bauer, Pieve di Cento (IT)

(73) Assignee: Allegiance Corporation, Mcgaw Park, IL (US)

( * ) Notice: Subject to any disclaimer, the term of this patent is extended or adjusted under 35 U.S.C. 154(b) by 0 days.

(21) Appl. No.: 10/355,504

(22) Filed: Feb. 3, 2003

(65) Prior Publication Data

US 2003/0163062 A1 Aug. 28, 2003

Related U.S. Application Data

(63) Continuation of application No. 09/546,041, filed on Apr. 10, 2000, now abandoned, which is a continuation-in-part of application No. 09/266,953, filed on Mar. 12, 1999, now abandoned, which is a continuation of application No. 08/781,779, filed on Jan. 9, 1997, now Pat. No. 5,916,175.

(51) Int. Cl.[7] .............................................. A61B 10/00
(52) U.S. Cl. ........................ 600/567; 600/564; 606/167
(58) Field of Search ................................. 600/564–567; 606/167, 170, 172; 604/22, 27, 164.01, 164.11, 164.12

(56) References Cited

U.S. PATENT DOCUMENTS

| | | | | |
|---|---|---|---|---|
| 4,958,625 A | * | 9/1990 | Bates et al. | 600/567 |
| 5,036,860 A | * | 8/1991 | Leigh et al. | 600/567 |
| 5,127,419 A | * | 7/1992 | Kaldany | 600/567 |
| 5,313,958 A | * | 5/1994 | Bauer | 600/567 |
| 5,916,175 A | * | 6/1999 | Bauer | 600/567 |

\* cited by examiner

*Primary Examiner*—Charles Marmor
(74) *Attorney, Agent, or Firm*—Andrew G. Rozycki

(57) ABSTRACT

The invention relates to a biopsy device having the ability to adjust the size of the sample to be removed. The biopsy device includes biopsy needle assembly and cannula insertion guide co-axially aligned therewith such that longitudinal adjustment of the cannula insertion guide likewise adjusts the exposure of the stylet and cutting edge of the biopsy needle assembly thereby changing the size of the resulting sample. A longitudinal adjusting element is positioned between and connects the cannula insertion guide and housing of the device. The invention is particularly useful in biopsy procedures where improved control over sample size and cutting stroke are desirable.

15 Claims, 2 Drawing Sheets

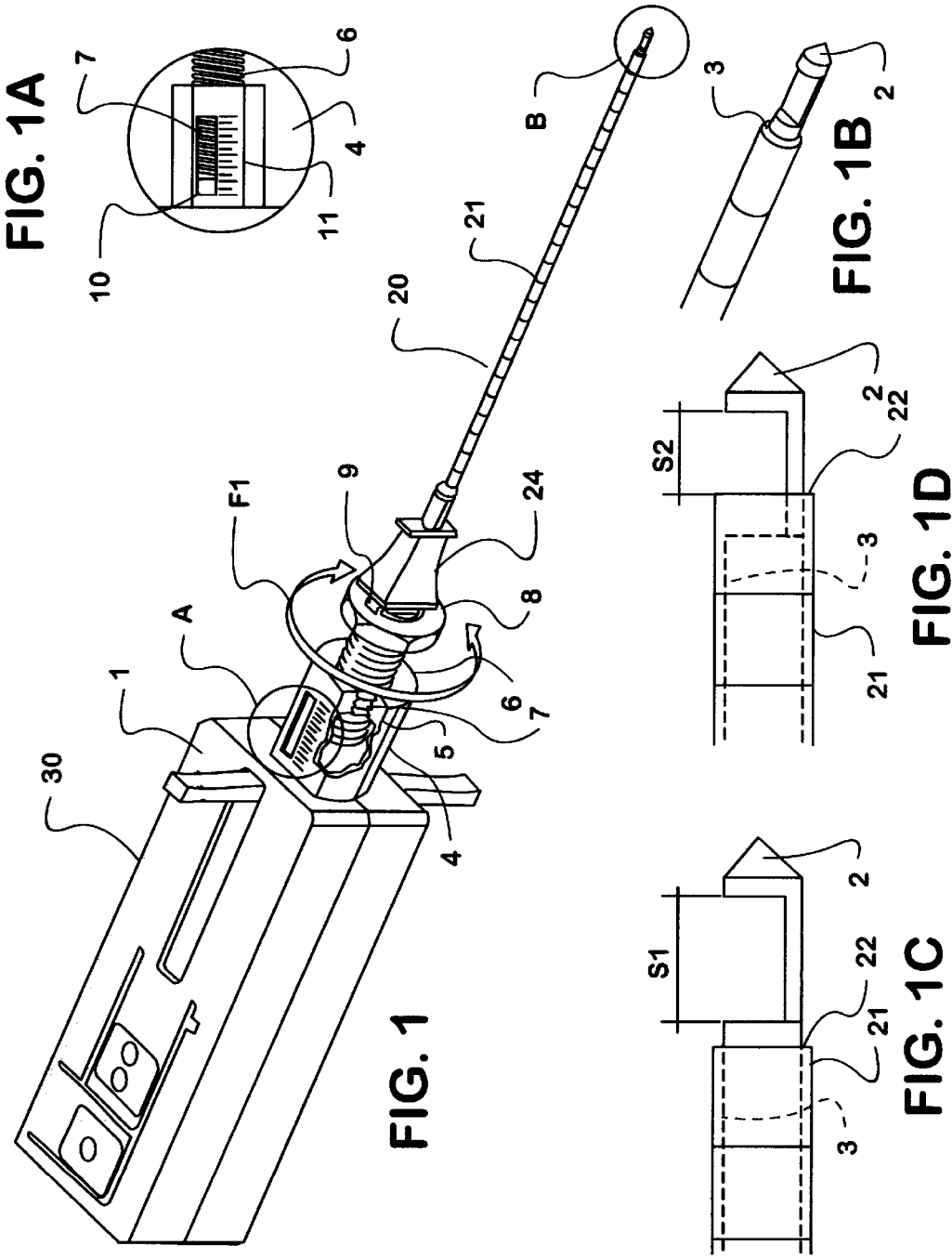

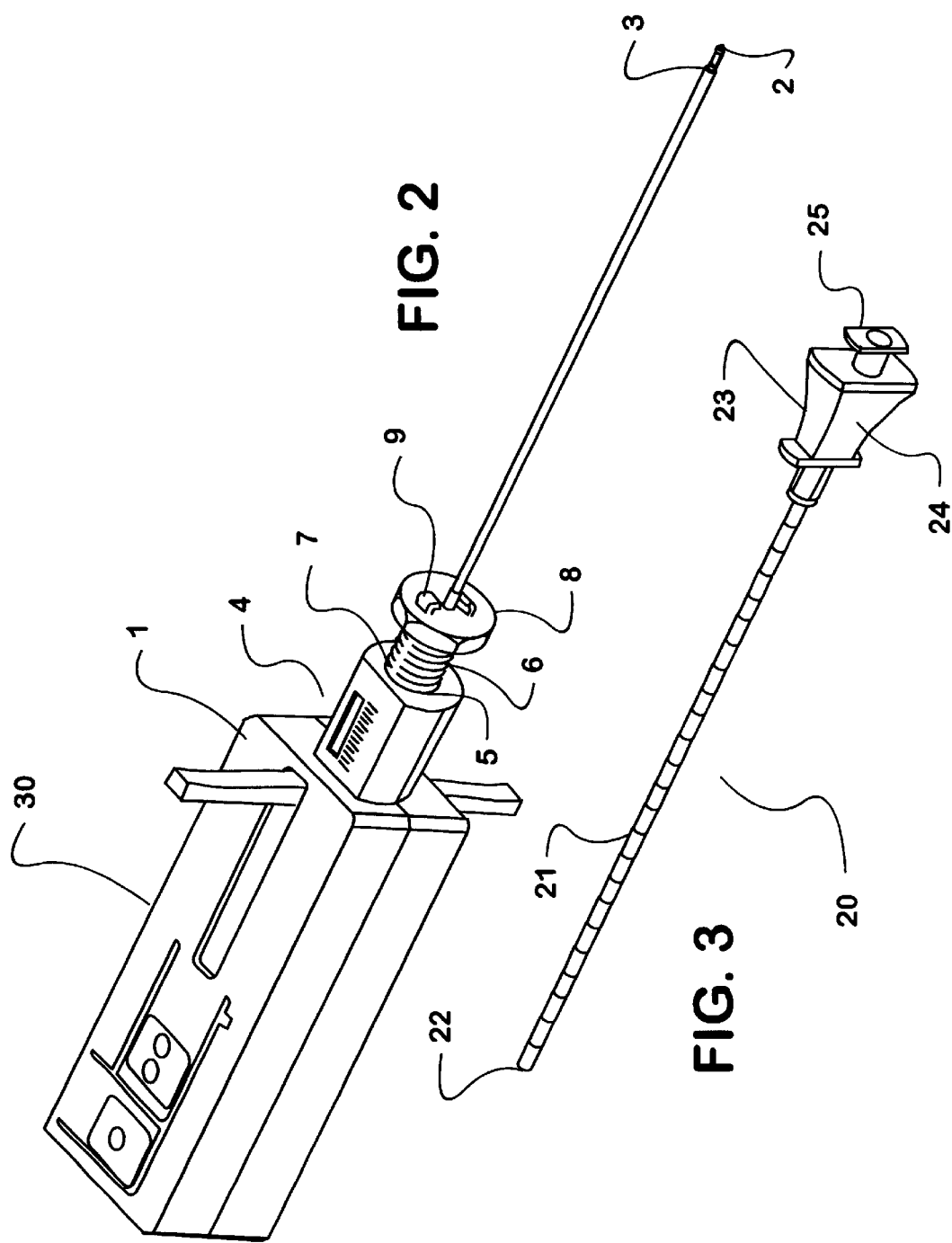

BIOPSY DEVICE WITH ADJUSTABLE SAMPLING

CROSS-REFERENCE TO RELATED APPLICATIOINS

This application is a continuation of U.S. patent application Ser. No. 09/546,041 filed on Apr. 10, 2000, now abandoned, which is a continuation in part of U.S. patent application Ser. No. 09/266,953 filed Mar. 12, 1999, now abandoned, which is a continuation of U.S. patent application Ser. No. 08/781,779 filed Jan. 9, 1997, now U.S. Pat. No. 5,916,175 issued Jun. 29, 1999.

FIELD OF THE INVENTION

The invention relates to a device for tissue removal in biopsy procedures. In particular, the invention relates to a manually operated biopsy device containing an adjustable biopsy needle.

BACKGROUND OF THE INVENTION

Biopsy needle devices with handpieces containing an actuating apparatus which activates the motion of a biopsy needle are known. For example, U.S. Pat. No. 4,958,625 to Bates et al. discloses a biopsy device containing a handpiece and stylet which projects independently of a cannula and wherein the handpiece contains an attachment means for the cannula. The insertion guide used in such systems includes a cannula guide made up of a hollow small tube in which the proximal end bears a trigger, and is equipped with an attachment means, as well as a luer lock for a syringe to introduce a medicament to the site after tissue removal.

Procedures using actuated biopsy needles typically involve first inserting the biopsy needle and cannula insertion guide into the patient's body by positioning the distal end of the needle in proximity to the object to be sampled. Upon determining the desired position by magnetic resonance (CAT scan) or other technique, the stylet and cannula cutting edge are sequentially activated to obtain the sample. Once the sampling step has been performed, the attachment means are released and the biopsy needle withdrawn from the cannula insertion guide to check the sample. If the sample is incorrect or otherwise insufficient, a new biopsy needle is inserted into the cannula insertion guide and the sampling sequence is repeated. After obtaining the desired sample, a medicament can be administered to the site by applying a syringe to the insertion guide.

One disadvantage of such systems is that variation or adjustments of sample length and needle cutting stroke are not feasible, since the stylet or cannula cutting edge are not adapted to adjust feed stroke beyond the tip of the insertion guide. Control of biopsy procedures is important when the tissue to be sampled is in proximity to vital organs or bones and positioning of the insertion guide or biopsy needle is such that the feed stroke of the stylet and cannula-cutting edge can potentially further damage the vital tissues, organs or bone.

There is a need in the biopsy device field for devices having improved control capabilities to permit the practitioner to avoid unnecessary tissue damage as well as obtain tissue samples with more specific parameters.

SUMMARY OF THE INVENTION

The invention disclosed is an adjustable biopsy device having the ability to vary the size of the sample to be removed. The biopsy device includes biopsy needle assembly and cannula insertion guide co-axially aligned therewith such that longitudinal adjustment of the cannula insertion guide likewise adjusts the exposure of the stylet and cutting edge of the biopsy needle assembly thereby changing the size of the resulting sample. The cannula insertion guide is connected to the housing of the device through a longitudinal adjusting element. The invention is particularly useful in biopsy procedures where improved control over sample size and cutting stroke are desirable.

The biopsy device generally contains a biopsy needle assembly, a housing having a control device for operation of the biopsy needle assembly therein, a cannula insertion guide co-axially aligned with and accommodating a portion of the biopsy needle assembly, and a longitudinal adjusting element positioned between (and connecting) said housing and insertion guide. The longitudinal adjusting element is adapted to adjust the position of the cannula insertion guide lengthwise relative to the biopsy needle assembly of the device. The housing containing the control device is generally configured as a handpiece and the control device per se is manually operated by the user or practitioner and actuates the biopsy needle assembly therein.

The biopsy needle assembly extends beyond the distal portion of the housing and includes a perforating stylet having proximal and distal portions which is positioned within a cannula having a cutting edge. The proximal portion of the perforating stylet is coupled to and operates relative to the cannula (and cutting edge) as activated by the control device within the housing. The medial portion of the stylet extends beyond the distal portion of the housing and co-axially through both the longitudinal adjustment element and the cannula insertion guide attached thereto. The distal portion of the stylet is positioned at the distal portion of the cannula insertion guide and contains an indentation (or groove) to accommodate and retain tissue.

The cannula insertion guide comprises a proximal attachment means adapted for removable attachment to the distal portion of the longitudinal adjustment element and for internal positioning of the biopsy needle assembly of the device. The cannula insertion guide and biopsy needle assembly are configured to operatively interact with one another such that the cannula cutting edge and perforating stylet of the biopsy needle assembly function at the distal tip of the cannula insertion guide. Rapid sequential motion between the stylet and cannula cutting edge beyond the distal tip of the cannula insertion guide severs or cuts the tissue to be sampled. The extent to which the biopsy needle assembly (cannula cutting edge and perforating stylet) extend beyond the distal tip of the cannula insertion guide is controlled by the longitudinal adjusting element of the device.

The longitudinal adjustment element is positioned between (and connects) the distal portion of the housing and the proximal portion of the cannula insertion guide and contains a lumen adapted for placement of the biopsy needle assembly therein. The longitudinal adjusting element has a proximal portion and distal attachment means, the proximal portion being adapted for engagement with and movement (e.g., rotatable motion) relative to the distal portion of the housing and the distal attachment means being adapted for removable attachment to the proximal attachment means of the cannula insertion guide such that adjustment of the longitudinal adjusting element results in corresponding adjustment of the cannula insertion guide in the same direction. In operation, the adjustment of the cannula insertion guide and corresponding the distal exposure of the biopsy needle assembly controls the degree of exposure of the stylet indentation and thus controls the amount of tissue to be accommodated therein.

Thus, there is disclosed a biopsy device comprising a biopsy needle assembly having a perforating stylet within a cannula having a cutting edge; a housing having a control device for operation of the biopsy needle assembly; a cannula insertion guide co-axially aligned with and accommodating the biopsy needle assembly and having proximal attachment means; and longitudinal adjusting element positioned between the housing and cannula insertion guide and having a proximal portion and distal attachment means and a lumen adapted for placement of the biopsy needle assembly; wherein the longitudinal adjusting element is adapted to co-axially adjust the position of the cannula insertion guide relative to the biopsy needle assembly of the device.

In a further embodiment, there is disclosed a biopsy device according to the invention comprising a longitudinal adjusting element adapted for engagement with and rotational movement relative to the housing of the device. In yet another embodiment, there is disclosed a biopsy device according to the invention further comprising an indicator means for indicating position and longitudinal displacement of the cannula insertion guide relative to the housing.

There is also disclosed a method of obtaining a tissue sample having a pre-deteremined size from a tissue site using a biopsy device according to the invention comprising the steps of inserting and positioning the cannula insertion guide and biopsy needle assembly of the device in proximity to the tissue sampling site; and actuating the biopsy needle assembly to obtain the sample; wherein the sample size is determined prior to actuating the biopsy needle assembly by adjustment of the longitudinal adjusting element of the device.

The invention also includes a kit for performing biopsy procedures comprising the biopsy device according to the invention.

Among the advantages of the device according to the invention is that it permits the user or practitioner to vary needle cutting stroke and therefore vary sample size. Another advantage is that a single device can be used to obtain multiple samples of varying sizes. Yet another advantage of the invention is that unnecessary damage of tissues and organs can be avoided as a result of the improved control over the sampling procedure.

BRIEF DESCRIPTION OF THE DRAWINGS

The invention is further illustrated by the drawings below together with the numerical references which remain consistent throughout:

FIG. 1 is an overall perspective view of one embodiment of the assembled device according to the invention.

FIG. 1A is a detailed view of one embodiment of the longitudinal adjustment element of the device as positioned in the housing and having indicating means.

FIG. 1B is a detailed view of one embodiment of the distal portions of the biopsy needle assembly and cannula insertion guide of the device according to the invention.

FIGS. 1C and 1D together schematically depict the adjustment of the biopsy needle assembly of the device relative to the cannula insertion guide which will produce different sample sizes after adjustment of the device.

FIG. 2 is a perspective view of one embodiment of the device according to the invention without the cannula insertion guide attached thereto.

FIG. 3 is a perspective view of the cannula insertion guide portion of the device.

DETAILED DESCRIPTION OF THE INVENTION

The biopsy device according to the invention is shown assembled in FIG. 1 and depicted with the cannula insertion guide detached in FIG. 2, the cannula insertion guide shown separately in FIG. 3.

In general, the biopsy device 30 includes a housing 1 containing a control device (not shown) for operating the biopsy needle assembly (which contains the perforating stylet 2 positioned within a cannula with cutting edge 3), a cannula insertion guide 20, and longitudinal adjusting element 6 positioned between the distal portion 4 of the housing 1 and the proximal portion 23 of the cannula insertion guide 20.

The stylet of the biopsy needle assembly of the device contains an indentation (or groove) located near the distal portion of the stylet proximal to the tip 2 which permits encroachment of the tissue to be sampled when the biopsy needle portion is positioned in proximity to the tissue to be sampled. Typically, the stylet contains a tip configuration which facilitates perforation or piercing through tissue to reach the site. Referring now to FIG. 1B, the distal tip of the stylet 2 is shown in an extended position with the stylet indentation fully exposed beyond both the cannula cutting edge 3 and distal portion of the cannula insertion guide 20.

The control device (not shown) for operation of said biopsy needle assembly can comprise any suitable manually operated actuating mechanism adapted to co-axially, sequentially and rapidly move or displace the stylet relative to the cannula cutting edge. For example, a spring-loaded assembly with a trigger mechanism can be used.

As can be seen in FIG. 3, the cannula insertion guide 20 includes a cylindrical hollow cannula 21 having proximal and distal ends, 23 and 22 respectively, and is adapted for co-axial alignment and internal accommodation and placement of the biopsy needle assembly of the device. The proximal portion 23 of the cannula insertion guide 20 can be of any suitable configuration or structure provided it includes a proximal attachment means. In a preferred embodiment, the proximal attachment means of the cannula insertion guide is a removable attachment means, i.e., one which can be reversibly detached from and mechanically compatible with the corresponding attachment means positioned on the longitudinal adjusting element 6. In one embodiment and as shown in the figures, the proximal portion 23 of the cannula insertion guide 20 comprises a tang 24 and attachment means in the form of a twist lock component 25 adapted for engagement with the corresponding receiving component 8 of the distal attachment means 9 located on the longitudinal adjusting element 6 of the device.

Various attachment systems can be used in accordance with the invention to couple the cannula insertion guide to the longitudinal adjusting element provided they together enable continuity of placement for the biopsy needle assembly therethrough. Examples of suitable attachment systems include, but are not limited to, a luer lock assembly, superimposed fitting components, channel and groove, screw-type assembly, and the like.

The longitudinal adjusting element 6 of the device is positioned between the distal portion 4 of the housing 1 and the proximal portion 23 of the cannula insertion guide 20 and includes proximal portion and distal attachment means 9 and a lumen (not shown) adapted for placement of the biopsy needle assembly. The longitudinal adjusting element 6 is adapted to co-axially adjust the position of the cannula insertion guide 20 relative to the biopsy needle assembly of the device.

The longitudinal adjusting element and distal portion of the housing can be configured in a variety of ways to accomplish the same result provided the longitudinal adjusting element can be incrementally and controllably adjusted in a precise manner. In a preferred embodiment and as shown in the figures, the longitudinal adjusting element 6 of the device comprises a threaded body 7 adapted for engagement and rotatable movement with a threaded channel 5 located in the distal portion 4 of the housing. In other words, the longitudinal adjusting element can be in the configuration of a screw-like component which adjusts the space between the cannula insertion guide 20 and the housing 1 upon rotation as shown by arrow F1 in FIG. 1.

In a further embodiment, the biopsy device of the invention further comprises an indicating means. The indicating means according to the invention can comprise any suitable structure, indicia or combination thereof which indicates the position and longitudinal displacement of the cannula insertion guide relative to the housing in an externally viewable manner. In one embodiment, the indicator means comprises one or a series of calibrated marking(s) on the housing from which to reference a point located on the longitudinal adjusting element of the device. The point located on the longitudinal adjusting element can be the truncated proximal end of the element or, alternatively, a viewable indicia or marking(s) located on the longitudinal adjusting element per se.

FIG. 1A illustrates one embodiment of an indicating means according to the invention. In this embodiment, externally viewable calibrated markings 11 are located on the body of the distal portion 4 of the housing 1 and are located proximate to a reading window 10, which permits a viewable reference to the proximal end of the longitudinal adjusting element 6. Accordingly, the markings 11 are calibrated to correspond to and measure the distance of the exposed stylet tip 2 beyond the distal end of the cannula 21 of the insertion guide 20, the practitioner can obtain a precise length of sample in operation.

FIGS. 1C and 1D together depict the biopsy needle assembly motion relative to the cannula insertion guide after adjustment of the device. FIG. 1C illustrates a first position of the device wherein the tip of the stylet 2 and indentation have been adjusted to obtain a full length sample. In this depiction, the stylet tip 2 and cannula cutting edge 3 are both extended beyond the distal tip 22 of the cannula 21 of the cannula insertion guide 20. When positioned within tissue and actuated, the cannula cutting edge 3 stroke will sever and obtain a sample having the size depicted as S1.

FIG. 1D illustrates the positioning of the distal end 22 of the cannula insertion guide 20 relative to the biopsy needle assembly after adjustment of the longitudinal adjusting element (not shown). Rotational movement of the longitudinal adjusting element with the cannula insertion guide attached thereto (as seen in FIG. 1, for example) in a direction away from the distal portion of the housing incrementally and precisely moves the distal end 22 of the cannula insertion guide 20 over the stylet thereby reducing the exposure of the indentation on the stylet and, thus, reduces the amount of tissue which contacts the stroke of the cutting edge 3. Accordingly, after insertion and actuation of the device, a sample having a size S2 is obtained which is smaller in comparison to a sample obtained prior to longitudinal adjustment.

The invention also includes a method of obtaining a tissue sample having a predetermined size from a tissue site using a biopsy device as described herein comprising the steps of a) inserting and positioning the cannula insertion guide and biopsy needle assembly of the device in proximity to the tissue sampling site, and b) actuating the biopsy needle assembly of the device to obtain a sample, wherein the sample size is determined prior to actuating the biopsy needle assembly by adjustment of the longitudinal adjusting element of the device.

In use, the practitioner can view the indicator means such as that depicted in FIG. 1A to determine the length of the cutting stroke of the biopsy needle assembly and makes the desired adjustment prior to actuating the device and obtaining the sample. Viewing the indicator means in conjunction with adjusting of the longitudinal adjusting element of the device allows the practitioner to obtain a sample of a particular size and, if circumstances require, avoid more damage than necessary to tissues surrounding the sampling site.

The components of the device can be made and assembled using various conventional materials, techniques and equipment known in the art. In general, the components of the device can be made from rigid materials such as plastics and metals and metallic alloys. Typically, the housing and some of the components of the control device for the biopsy needle assembly can be composed of plastic, whereas the cannula components and stylet can be composed of metals such as stainless steel. Components such as the longitudinal adjusting element, for example, can be composed of either plastic or metal.

The invention also includes a kit for performing biopsy procedures comprising the biopsy device according to the invention. In addition to the biopsy device as described herein, the kit can include those instruments and equipment which are typically associated with biopsy procedures. Examples of such instruments and equipment include, but are not limited to, syringes (and needles), local anaesthetics, microscope slides, scalpels, rulers, drapes, swabs, vials, labels, storage solutions, forceps, sponges, bandages, cups and wraps. Packaging or containers which house the biopsy device of the invention along with the other components used in the biopsy kit can also be included.

INDUSTRIAL APPLICABILITY

The present invention permits practitioners to increase the level of control during biopsy procedures. Accordingly, biopsies can be performed with the lesser extent of tissue damage and damage to surrounding areas as compared to conventional biopsy techniques, and can be performed with more precision in accordance with the practitioner's preferences and the patient's needs. Furthermore, a single device can be used to obtain a multitude of sample sizes.

The invention has been described with reference to various specific and preferred embodiments and techniques. However, it should be understood that reasonable variations and modifications are possible from the foregoing disclosure without departing from either the spirit or scope of the present invention as defined by the claims.

What is claimed is:

1. A biopsy device comprising:
   a) a biopsy needle assembly having a perforating stylet within a cannula having a cutting edge;
   b) a housing having a control device for operation of said biopsy needle assembly;
   c) a cannula insertion guide co-axially aligned with and accommodating said biopsy needle assembly and having a proximal attachment means; and
   d) a longitudinal adjusting element positioned between said housing and cannula insertion guide and having a proximal portion and distal attachment means and a lumen adapted for placement of said biopsy needle assembly;

wherein said longitudinal adjusting element is adapted to co-axially adjust the position of the cannula insertion guide relative to the biopsy needle assembly of the device.

2. A biopsy device according to claim 1 wherein the proximal portion of said longitudinal adjusting element is adapted for engagement with and movement relative to a distal portion of the housing.

3. A biopsy device according to claim 2 wherein said proximal portion is adapted for rotatable movement and comprises a threaded body for engagement within a threaded channel in the distal portion of the housing.

4. A biopsy device according to claim 1 further comprising an indicator means for indicating position and longitudinal displacement of the cannula insertion guide relative to the housing.

5. A biopsy device according to claim 4 wherein the indicator means comprises a viewable calibrated marking on the housing from which to reference a point located on the longitudinal adjusting element.

6. A biopsy device according to claim 1 wherein the proximal attachment means of said cannula insertion guide is adapted to removably attach the distal attachment means of said longitudinal adjusting element.

7. A method of obtaining a tissue sample having a predetermined size from a tissue site using a biopsy device according to claim 1 comprising the steps of:

a) inserting and positioning the cannula insertion guide and biopsy needle assembly of the device in proximity to the tissue sampling site; and b) actuating the biopsy needle assembly of the device to obtain a sample;

wherein the sample size is determined prior to actuating the biopsy needle assembly by adjustment of the longitudinal adjusting element of the device.

8. A kit for performing biopsy procedures comprising a biopsy device according to claim 1, in combination with at least one additional surgical component.

9. In a biopsy device having a housing and biopsy needle assembly wherein said housing has a control device for operation of the biopsy needle assembly, said biopsy needle assembly having a perforating stylet and a cannula cutting edge, the improvement comprising:

(a) a cannula insertion guide; and (b) a longitudinal adjusting element positioned between a distal portion of said housing and a proximal portion of said cannula insertion guide such that movement of the longitudinal adjusting element co-axially adjusts the position of the cannula insertion guide relative to the biopsy needle assembly.

10. A biopsy device according to claim 9 wherein a proximal portion of the longitudinal adjusting element is adapted for engagement with and rotational movement relative to the distal portion of the housing.

11. A biopsy device according to claim 10 wherein said proximal portion of the longitudinal adjusting element is threaded for rotational movement and engagement within a threaded channel in the distal portion of the housing.

12. A biopsy device according to claim 9 wherein the a proximal attachment means of the cannula insertion guide is adapted to removably attach a distal attachment means of the longitudinal adjusting element.

13. In a biopsy device comprising a housing and biopsy needle assembly wherein said housing has a control device for operation of the biopsy needle assembly, said biopsy needle assembly having a perforating stylet and a cannula cutting edge, the improvement comprising:

(a) a cannula insertion guide; and (b) a longitudinal adjusting element positioned between a distal portion of said housing and a proximal portion of said cannula insertion guide such that movement of the longitudinal adjusting element co-axially adjusts the position of the cannula insertion guide relative to the biopsy needle assembly; and (c) an indicator means for indicating position and longitudinal displacement of said cannula insertion guide relative to the housing.

14. A biopsy device according to claim 13 wherein the indicator means comprises viewable indicia located on the distal portion of the housing and a reference point located on the longitudinal adjusting element.

15. A biopsy device according to claim 13 wherein a proximal attachment means of the cannula insertion guide is adapted to removably attach a distal attachment means of the longitudinal adjusting element.

* * * * *